(12) United States Patent
Charette et al.

(10) Patent No.: US 8,571,181 B2
(45) Date of Patent: Oct. 29, 2013

(54) RAPIDLY SWITCHING DUAL ENERGY X-RAY SOURCE

(75) Inventors: Colin Charette, Encinitas, CA (US); David Reynolds, Loveland, CO (US)

(73) Assignee: XRSciences LLC, Encinitas, CA (US)

( * ) Notice: Subject to any disclaimer, the term of this patent is extended or adjusted under 35 U.S.C. 154(b) by 381 days.

(21) Appl. No.: 12/917,973

(22) Filed: Nov. 2, 2010

(65) Prior Publication Data
US 2011/0103554 A1    May 5, 2011

Related U.S. Application Data

(60) Provisional application No. 61/280,216, filed on Nov. 2, 2009.

(51) Int. Cl.
| *H01J 35/14* | (2006.01) |
| *H01J 35/06* | (2006.01) |
| *H01J 35/30* | (2006.01) |

(52) U.S. Cl.
USPC .................. 378/137; 378/134; 378/136

(58) Field of Classification Search
USPC ............... 378/4–20, 62, 91, 101, 111, 112, 378/114–116, 119, 121, 134, 136, 137, 145, 378/204, 210; 250/370.01, 370.08, 370.09, 250/371
See application file for complete search history.

(56) References Cited

U.S. PATENT DOCUMENTS

| 2,720,607 | A | * | 10/1955 | Criscuolo et al. ............. 378/136 |
| 6,188,747 | B1 | | 2/2001 | Geus et al. |
| 7,529,344 | B2 | | 5/2009 | Oreper |
| 7,852,979 | B2 | * | 12/2010 | Edic et al. ....................... 378/16 |
| 2002/0034279 | A1 | * | 3/2002 | Hirano et al. ................ 378/114 |
| 2004/0247082 | A1 | * | 12/2004 | Hoffman ....................... 378/119 |
| 2006/0153335 | A1 | * | 7/2006 | Ishikawa et al. .............. 378/101 |
| 2008/0260101 | A1 | * | 10/2008 | Oreper ......................... 378/134 |
| 2010/0104062 | A1 | * | 4/2010 | Wu et al. ........................ 378/19 |
| 2010/0183117 | A1 | * | 7/2010 | Tsumuraya et al. .............. 378/9 |

FOREIGN PATENT DOCUMENTS

| JP | 2000-040478 A | 2/2000 |
| JP | 2007-042516 A | 2/2007 |
| JP | 2007-265917 A | 10/2007 |
| WO | 2009-011422 A1 | 1/2009 |

OTHER PUBLICATIONS

International Search Report and Written Opinion issued on Jul. 8, 2011, in corresponding application No. PCT/US2010/055108, 8 pages.

* cited by examiner

*Primary Examiner* — Anastasia Midkiff
(74) *Attorney, Agent, or Firm* — Procopio, Cory, Hargreaves & Savitch LLP

(57) ABSTRACT

A dual energy X-ray source for use in Homeland Security, Medical, Non-destructive Testing, and other markets includes a power supply, and a single x-ray tube. The X-ray tube includes two cathodes, and a single anode. The electrons from the cathodes travel predominantly along the axis of the x-ray tube, and impact the anode. The grid and/or focus coil direct the electrons so that electrons can pass by the cathode. The cathodes are kept at different potential, such that the tube can rapidly switch energies, and can rapidly switch output flux from each cathode.

20 Claims, 29 Drawing Sheets

RAPIDLY SWITCHING DUAL ENERGY X-RAY SOURCE

RELATED APPLICATIONS

This application claims the benefit of U.S. Provisional Patent Application Ser. No. 61/280,216, filed Nov. 2, 2009, entitled "Multi Energy X-ray Source" which is hereby incorporated by reference in its entirety.

BACKGROUND OF THE INVENTION

1. Field

This invention relates to X-ray apparatus which are capable of switching emission levels and more particularly to an X-ray tube system which can rapidly switch emission levels so that the tube can be use for imaging, fluorescence, and other applications using differing energies.

2. Background of the Invention

In the Homeland Security industry, dual energy X-ray is used for screening of carry-on baggage, screening of checked baggage, and screening of cargo. The use of Dual Energy X-ray for Homeland Security allows users to distinguishing different materials, aiding in the detection of contraband, explosives, and illicit material as well as in the identification of materials in the object being scanned.

Dual energy X-ray is used in the medical industry for dual energy computed tomography (CT), dual energy X-ray absorptiometry, dual energy imaging, and other applications. Besides the Homeland Security and medical markets, dual energy X-ray is used in the non-destructive testing, dental, food packaging, coal, and other industries.

There are several methods of producing dual energy X-rays and conducting dual energy analysis. In the simplest form, two or more detectors are used, one behind the other, and a filter is placed between the detectors. One detector receives one energy range, and the other detector receives a second energy range due to the filter. Alternately, an energy discriminating detector can be used to separate energies, such as a CZT detector. Another approach commonly used is to vary the end output energy of the X-ray source, so that the X-ray source emits two or more X-ray energy ranges. Yet another approach is to use more than one X-ray tube, and each X-ray tube emits one or more energy ranges.

Desirable characteristics for a dual energy source are fast switching speeds between energies, high stability, small form factor, simplicity, lowest system cost, long life, high reliability, and the ability to rapidly change the flux for each separate energy. Having the same focal spot location is also highly desirable for some applications. The exact combination of characteristics that is the most valuable depends on the application.

Several approaches have been developed or proposed that have some but not all of these characteristics.

One approach involves using two or more separate X-ray tubes, and running each source independently. This provides rapid switching speeds. The problem with this approach is that it takes up the space of two X-ray sources, and each source has a different focal spot location. Thus the solution is relatively large, and produces two different focal spot locations. In imaging applications, complexity, alignment and misregistration between the images is another issue with using two separate sources.

An alternate solution detailed in U.S. Pat. No. 5,661,774, is to use electronics that rapidly switch energies of the X-ray tube. An application of this would be in dual energy CT in medical and Homeland Security application where rapid switching is desirable. An issue with this approach is the difficulty in switching the X-ray energy at high speed. This requires complex electronics, drives up system costs and is not optimum for tube life. Another issue with this approach is that the rapid switching induces variation in the output energy of the X-ray source.

U.S. Pat. No. 6,188,747 details an x-ray source that uses two independent anodes, and two cathodes. Thus it has two x-ray sources in one X-ray tube, resulting in increased cost, complexity, weight, and shielding. The limitation of this approach is the physical size of the unit, and the spot size location being different for each anode.

An approach that solves the spot location problem is to use two cathodes and one anode in the X-ray source, and to physically separate the cathodes. This is detailed in U.S. Pat. Nos. 7,529,344 and 7,792,241 and is illustrated in FIG. 17. The cathodes 1 are at different energies, and the cathodes 1 are separated, so the cathodes 1 do not arc. With this solution, each cathode 1 has a separate grid 3. A limitation with this approach is the difficulty in alignment of the cathode 1 and grids 3 and even more difficult, alignment of the 2 spots. Yet another issue is the physical size of the resulting X-ray tube.

BRIEF SUMMARY OF THE INVENTION

In one embodiment, an improved X-ray source that overcomes the limitations of the sources outlined previously is provided. This source can provide rapid switching speeds between energies, can fit the same or similar from factor to conventional single energy sources, can rapidly vary the output flux of the source, is rugged, optimizes life, minimizes voltage gradients, and if required, the output flux and energy can be highly stable.

In an embodiment for dual energy x-rays, the source uses two cathodes, and a single anode in a chamber, such as a tube. The cathodes emit electrons, and the electrons from each cathode travel in the direction of the axis of the X-ray source to impact the anode.

Electrons from the cathode farthest from the anode emits electrons that travel in the direction of the axis of the tube and pass through or by the cathode closer to the anode. The direction of the electrons is influenced by the grid and/or the focus of the cathode farthest from the anode and the cathode, grid and/or focus closest to the anode. These electrons travel past the second cathode and impact the anode. Electrons from the second cathode (closest to the anode) are emitted, and travel largely down the central axis of the X-ray tube. The grid and/or focus closest to the anode influence the direction of the electrons coming from this cathode. Controlling grids and/or focus allows for adjustments of the spot size and spot location, as well as adjustment of the flux for each energy range of the X-ray source.

BRIEF DESCRIPTION OF THE DRAWINGS

The accompanying drawings are not intended to be drawn to scale. In addition, the drawings are simplified for explanation purposes.

FIG. 6 shows a side view of the new source, but with cathodes located on the side of the tube as shown.

FIG. 7 shows the source with a rotating anode.

FIG. 8 shows a rotating anode that has different materials, so that the source can vary both the energy, and the target material.

FIG. 9 shows the new source, using a scanning mechanism to move where the electrons impact the target (thus moving the location where the resulting X-ray are emitted). The target and scanning can be along a line, circular, multiple positions, or whatever shape is advantageous to scan. Deflection plates or coils 14 are used to direct the electrons to the desired location(s).

DETAILED DESCRIPTION OF THE INVENTION

In one embodiment, the following invention is directed towards dual energy x-ray sources that are used in the medical, security or other industries that use dual energy or multi-energy X-ray sources are used. Applications include both imaging and non-imaging devices that use dual or multi-energy range X-ray sources. However, one skilled in the art will appreciate that the implementation can be employed for the conversion of other devices that accelerate positively or negatively charged atomic or subatomic particles or ions, hereafter referred to as particles.

Note that in the following description, anode, grid, cathode, and focus are used. There are various definitions of grid, anode, cathode and focus which can vary by industry. In this document, the cathode is defined as the item that emits electrons (or particles). The cathode may include a filament, or the cathode may be just a filament. Numerous types of cathodes are known and used in x-ray sources such as thermionic, cold, solid state, nanotubes, crystal-based, optical, etc. The anode is defined as the item that the electrons (or particles) predominantly impact. A number of different material are often used for the anode, including W, Mo, Cu, Rh, Ni, Cr, Co, Fe, Re, Pd, Ru, Pt, V, Ta, Au, Ag, etc. The anode and cathode do not necessarily have to be solid, they can be a gas or a plasma. The electrons (or particles) travel from the cathode to the anode. The grid is defined as the item(s) that controls the number of electrons (or particles). For example, it can turn the number of electrons on or off, or control the number of electrons coming from the cathode. The grid can also be used to influence the path of the electrons (or particles). The focus (not shown) is defined as the item(s) that shapes or influence the direction of the electrons, and typically this is used as a lens to focus the electrons. In some cases, the focus can also be used to both control the number of electrons and to influence the direction of the electrons. In this case, it is acting partially as a grid and partially as a focus as it is controlling the number and direction of the electrons. For very rapid switching, the grid and focus can also be synchronized to control the numbers of electrons. It therefore should be noted that in this patent the use of grid, anode, cathode and focus are defined in terms of their operation, and should not be limited by strict technical definitions used in some industries. It will be appreciated that the terms flow and movement may be used to describe control of the number of charged particles, the direction and path of the particles, or both.

Figure 1:
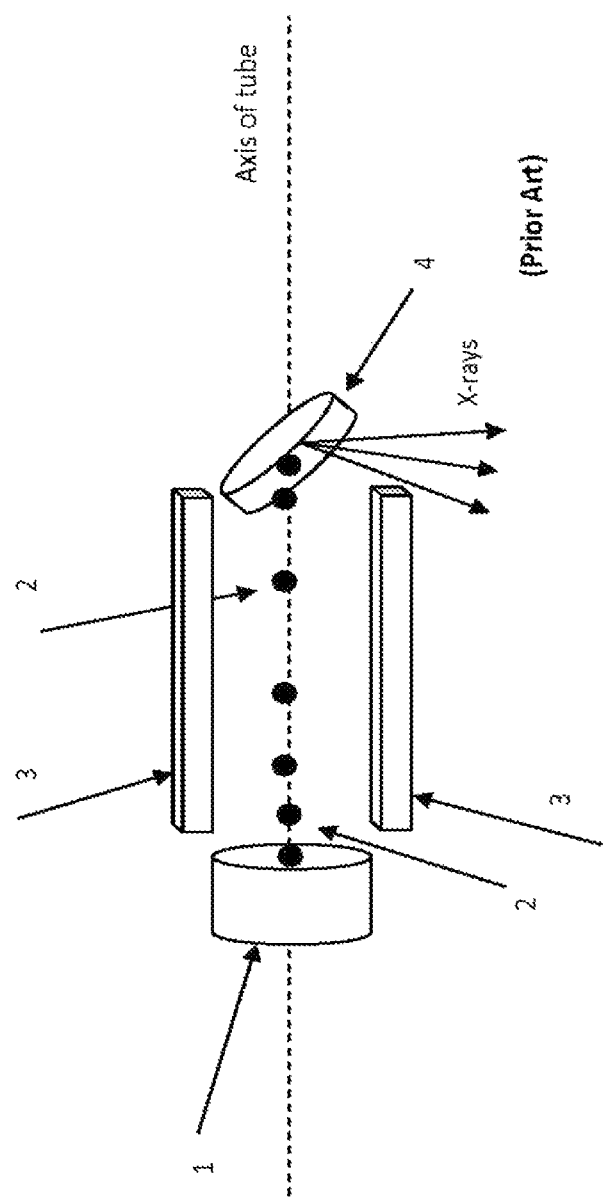
FIG. 1 shows a conventional x-ray source, showing electrons flowing from the cathode to the anode.

FIG. 1 illustrates a conventional x-ray generator. This consists of the cathode 1, the anode 4, and a grid electrode 3. Not shown is a focus electrode, but each cathode may have zero, one or more focus electrodes. The electrons 2 travel from the cathode to the anode. The electrons predominantly travel down the axis of the tube, and impact the anode. The grid is used to control the electron flow and may be used to influence the direction of the electrons. In this case the particles are electrons, but any charged particle can be used. For example, deuterium or tritium ions can be used for generating Neutrons.

Figure 2:
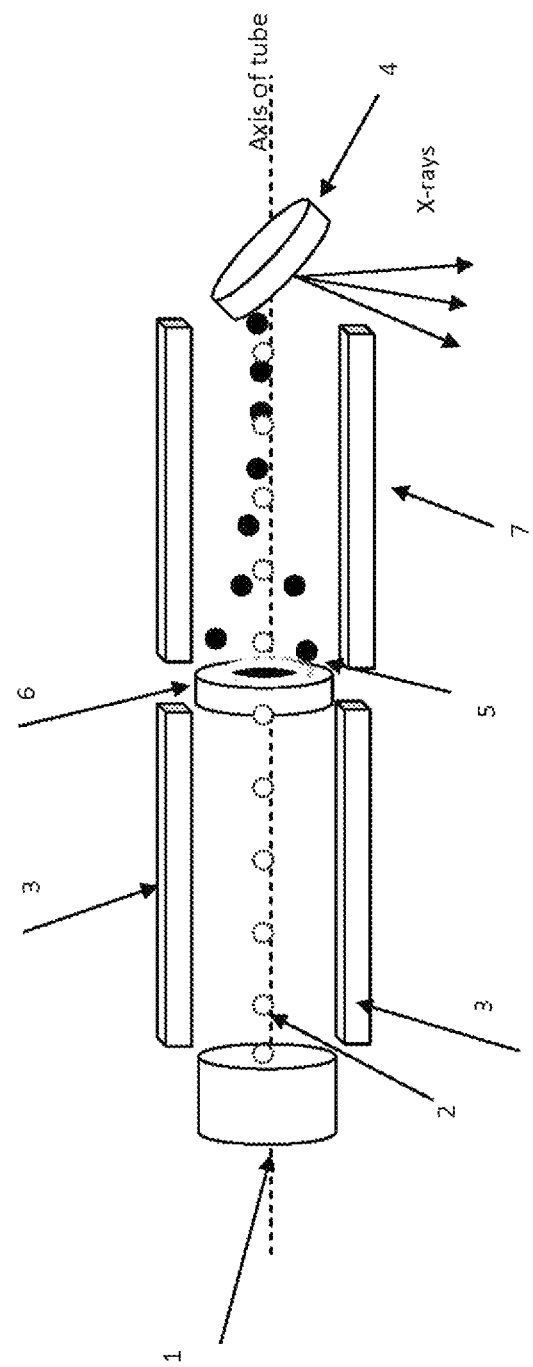
FIG. 2 shows a side view of the new x-ray source, with two cathodes.
Figure 3:
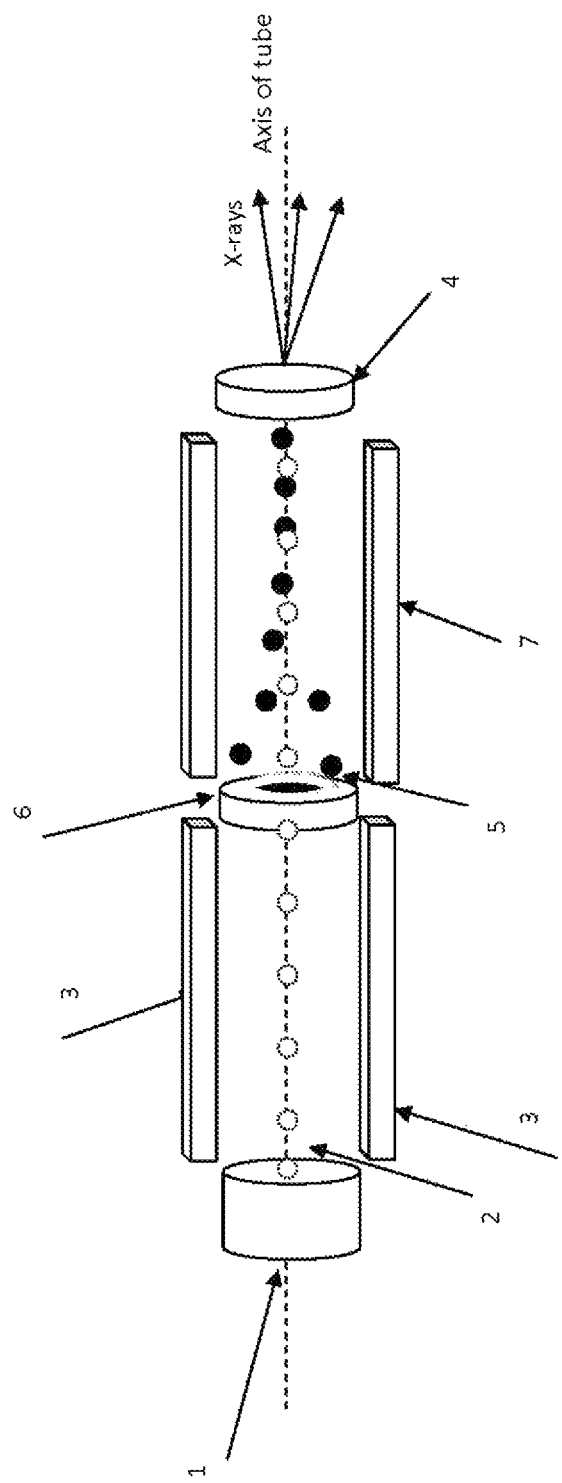
FIG. 3 shows a side view of the new source, but with a transmission target.
Figure 6:
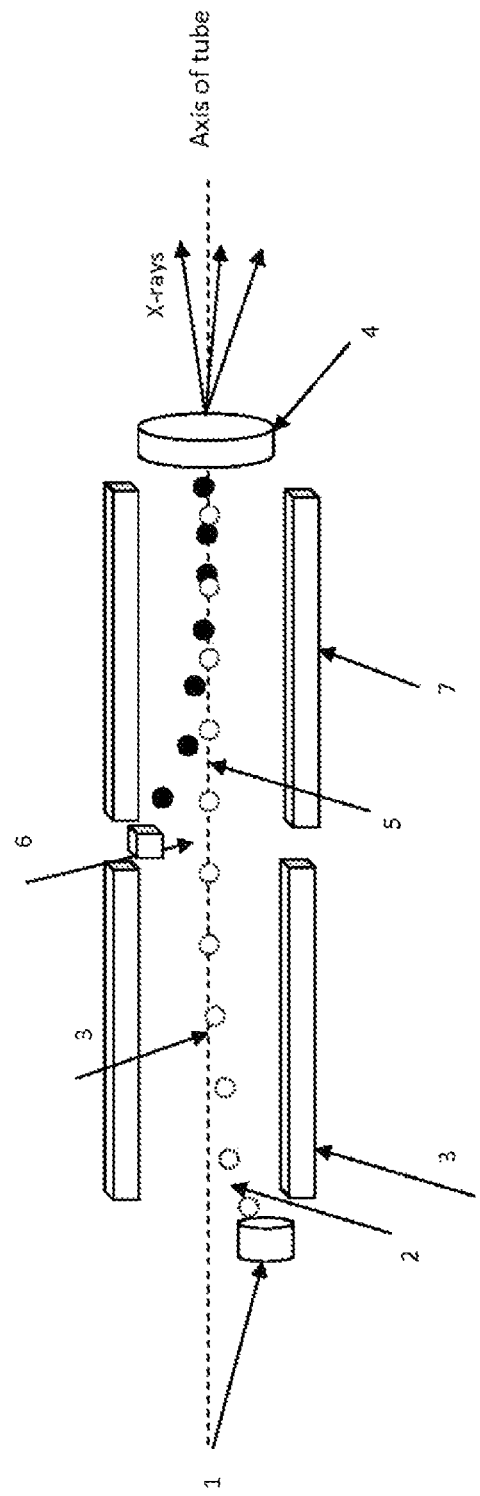
FIGS. 6 to 9 show variations of the X-ray source, to show possible different configurations that can be used. This is not intended to limit the possible modifications of the invention, but to show that there are a number of variations of the invention that can be derived by those skilled in the art.

FIG. 2 illustrates a preferred embodiment of the invention. The electrons 2 are emitted by the cathode 1. In this case, cathode 6 has a hole in the center of the cathode. The hole may be centered about the axis of the tube or chamber. Cathode 1 electrons 2 travel through cathode 6. The electron optics are designed such that some or all of the electrons do not impact cathode 6, but continue through cathode 6 towards the anode. The grid electrode, and/or focusing electrode are used to direct the electrons towards the central axis of the tube, so that the electrons pass through Cathode 6. One can appreciate that one skilled in the art can come up with many variations and approaches to control the electrons such that they are not stopped by cathode 6. In this example, Cathode 6 has a hole through the center. However, the Cathode can be positioned to the side, or off the axis of the chamber, as shown in FIG. 6, and the electrons from Cathode 1 will pass by Cathode 6, not through Cathode 6. In both cases, the electrons from both cathodes travel along the direction of the axis of the X-ray tube to the anode. Note that the system can be built without a grid, where the cathode provides the electrons, and the cathode or the focus can be used to control the number of electrons emitted.

Electrons continue past cathode 6, and impact the anode 4.

In the preferred embodiment, cathode 6 is at a different potential than cathode 1, and cathode 6 emits electrons 5, which impact anode 4. The grid 7 is used to control the flux from cathode 6, as well as shape the electron optics so the electrons 2,5 from both cathodes impact the anode. Alternately a combination of grid 7 and/or focus (not shown) can be used to shape the direction of the electrons 2,5. The electron optics can be used to focus the electrons such that there is overlap in the impact location on the anode 4. Alternately, the electron optics can produce a displacement between the spot locations if this is preferable. The shape, location, and size off the resulting spot from each cathode can be controlled with the electron optics.

In one embodiment, a DC power supply is used to power the grid and cathodes. Ideally one power supply is used that powers both cathodes and grids, or alternately, separate power supplies can be used. In the preferred embodiment, the power supply sets each cathode at fixed power levels. In the preferred embodiment, the power to the cathode is designed to be very stable and ideally controlled by closed loop. The power supply also sets suitable voltages on the grid and focus (when grid and/or focus are used). By varying the grid voltages, which in the preferred embodiment is controlled by the power supply, the output flow of electrons from the cathodes can be controlled. This approach provides the ability for very rapid switching, as well high reliability of the X-ray tube due to the constant power on the cathodes. Note that there are many variations possible to those skilled in the art, such as using one or more separate power supplies for each cathode and grid, using AC or DC to power any filament in the cathode, using a separate power supply to provide the variation to the grid, using different control mechanisms on the grid, using trigger mechanisms which are synchronous or asynchronous, and so forth.

It will be appreciated that control functionality of the power supply as described herein may be implemented as hardware, software, or a combination of the two. For example, a processor in communication with a non-transitory computer readable medium may be configured to implement a method for operating a charged particle source according to the description above. For example, the processor may be configured to apply voltages as described above in order implement the described functionality. In particular, the processor may cause the power supply to apply different voltage differentials to the cathodes, grids, and anode, in order to cause the flow of charged particles described above.

Figure 28:
FIG. 28 shows a pictorial view of a tungsten (or other material) coil that may be used for the cathode when shaped suitably.
Figure 29:
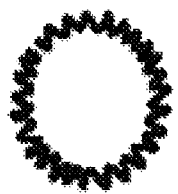
FIG. 29 shows a pictorial view of the coil in FIG. 28, but shaped in a circular fashion, according to an embodiment of the invention.

With regards to the cathode, cathode 1 can be a conventional cathode known by those skilled in the art, or it can be a cathode similar to cathode 6, 8. Cathode 6, 8 is designed so that the electrons pass by or through the cathode. Example of this cathode can include something as simple as tungsten wire, coil, single crystal or metal shaped like a washer. In the preferred embodiment, the approach would be to take tungsten wire, wrap it into a spring like a conventional filament as shown in FIG. 28, bend this into a circle similar to FIG. 29, mount this so that the ends are close, and to use several supports to hold the filament in place. Thicker tungsten wire can be used if a more rigid filament is desired.

The cathode does not have to use just a filament, or solid metal. Other approaches to generating the electrons can be used, such as taking a washer-shaped material, covering it with Cesium, and optically stimulating this with a laser. For very high performance and long life, another approach is to use a dispenser cathode, but shaped to allow the electrons to pass through or by the cathode. As can be appreciated, those skilled in the art can come up with many different approaches to building cathode 6, 8, and use various processes, such as high temperature processing, vacuum processing, and so forth to build and process the cathode.

Figure 4:
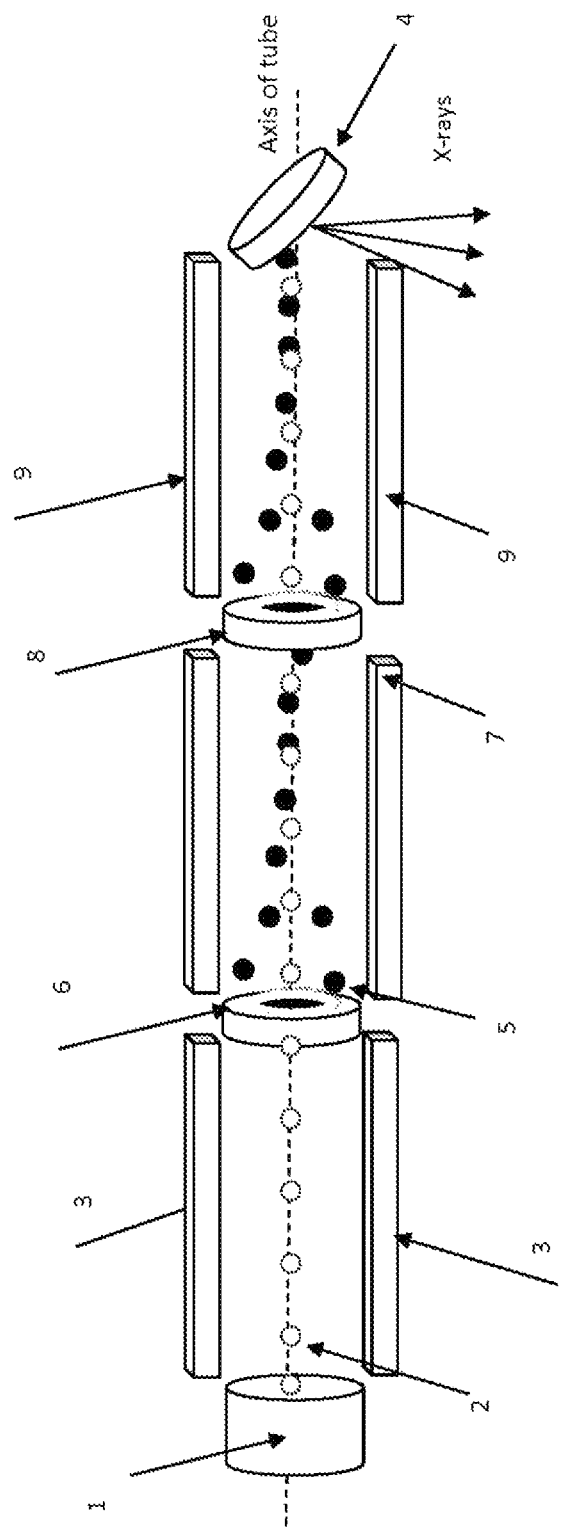
FIG. 4 shows a side view of the new source that can output multiple energies.
Figure 5:
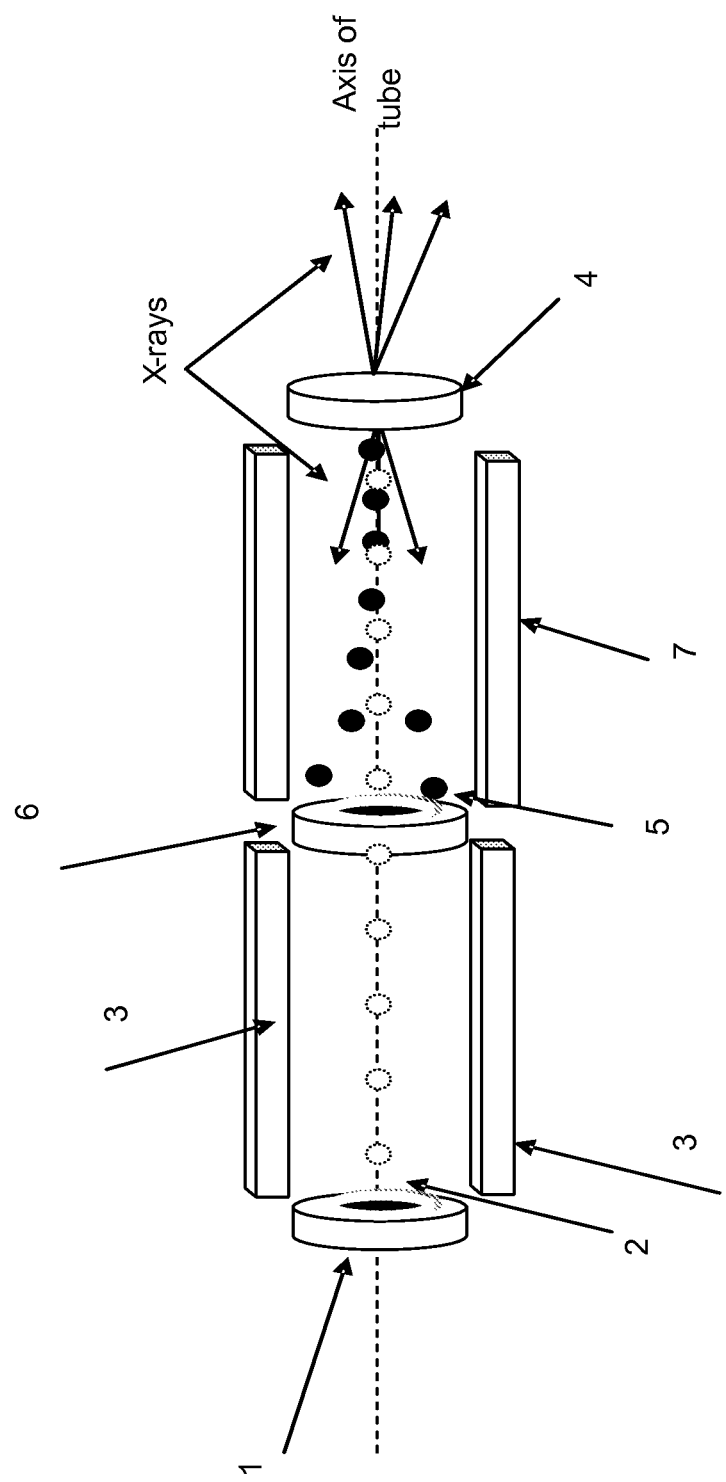
FIG. 5 shows a side view of the new source, with the x-ray flux traveling back through the source.

An example configuration for the X-ray tube would be of a tube emitting 160 Kv and 80 kv X-rays. Several configurations are possible. In this case, possible configurations include having cathode 1 at −160 Kv, cathode 6 at −80 kV, and the anode at ground. Alternately cathode 1 can be at ground, cathode 6 can be at +80 Kv, and the anode can be at +160 Kv. Yet another configuration is to have cathode 1 at −80 Kv, cathode 6 at ground, and the anode at +80 Kv. The output energy of the tube can be controlled by adjusting the potential between the cathodes and anode. Multiple energy output ranges, or further division of the acceleration regime is possible, by adding cathodes along the central axis as illustrated in FIG. 4. Output can be two, three, or more energies by using the same approach as detailed in FIG. 4. One skilled in the art can appreciate that the use of segmented accelerating regions can allow for a more controlled acceleration of the electrons, thus additional accelerating regions can be added to better control the electron acceleration.

In the preferred embodiment, the grid controls the flow of electrons from each cathode, as well as directs the electrons towards the central axis of the tube. In the preferred embodiment, a focus is also used to further focus the electrons towards the central axis of the tube. The grid and focus from cathode 6 will shape and focus electrons from both Cathode 6 and Cathode 1. Variations in this configuration are possible by those skilled in the art. For example, the grid can be used to both control and shape the direction of the electrons, such that a focus is not used.

The amount of flux from each energy range can be separately controlled, pulse to pulse, by varying the number of electrons emitted from each cathode. Normal operation would be by energizing one cathode, having the anode emit X-rays at one energy range, stopping the flow of electrons from this cathode, and then energizing the second cathode, resulting in X-rays from the second energy. In the preferred embodiment, this would be done using the grids to turn on and off the flow of electrons to the anode. As each cathode can be run independently, it is also possible to have electrons emitted by both cathodes simultaneously, resulting in X-rays of both energies being emitted simultaneously. Another method of varying the output flux, without using a grid, would be to vary, pulse to pulse (or at some other frequency) the number of electrons emitted by each cathode.

The benefit of this embodiment is that it overcomes many of the limitations of previous sources. The source can produce very rapid switching, can fit in the same or similar form factor to similar energy conventional X-ray tubes, can rapidly vary the amount of flux, and with a good generator has the potential to produce highly stable X-rays in terms of energy and flux. Another added benefit of this approach is that it is amenable to upgrading existing x-ray sources such that the new source can have identical or very similar form factors.

Figure 7:
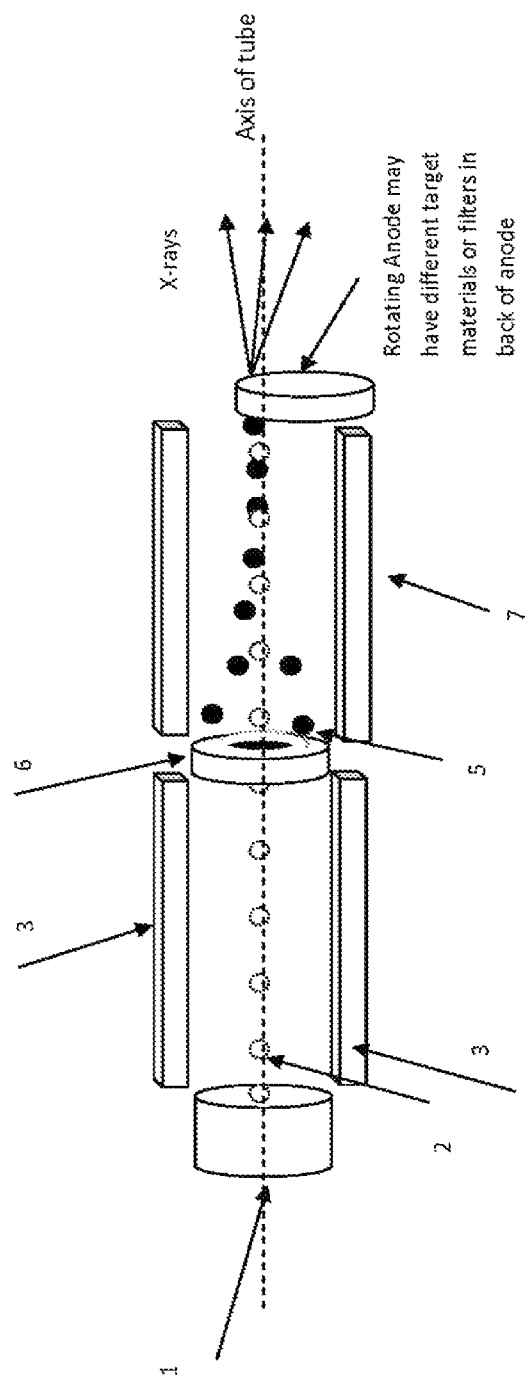
Figure 8:
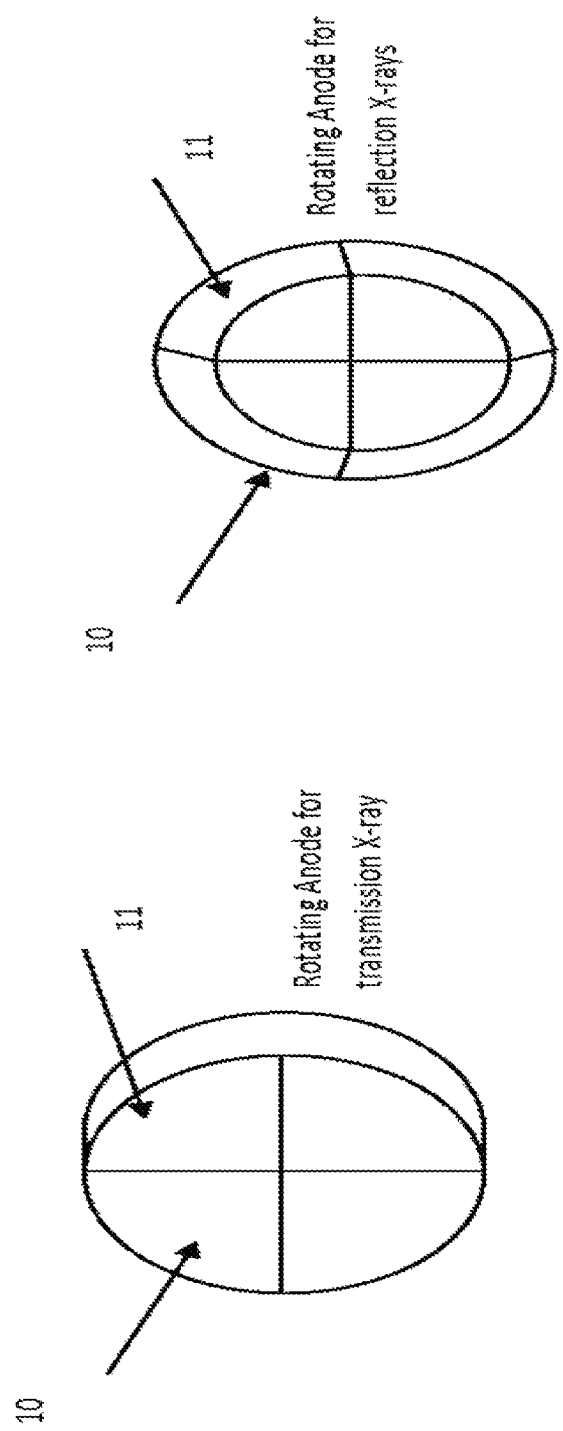
Figure 9:
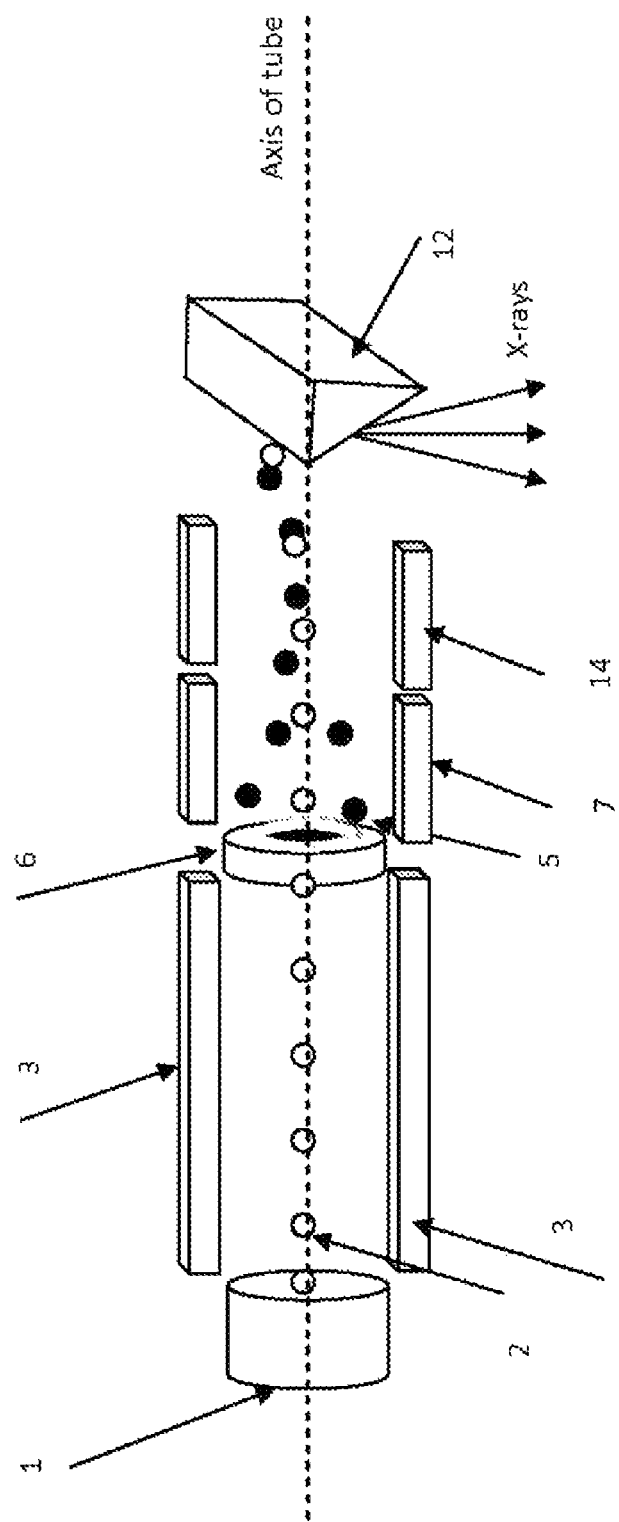
Figure 10:
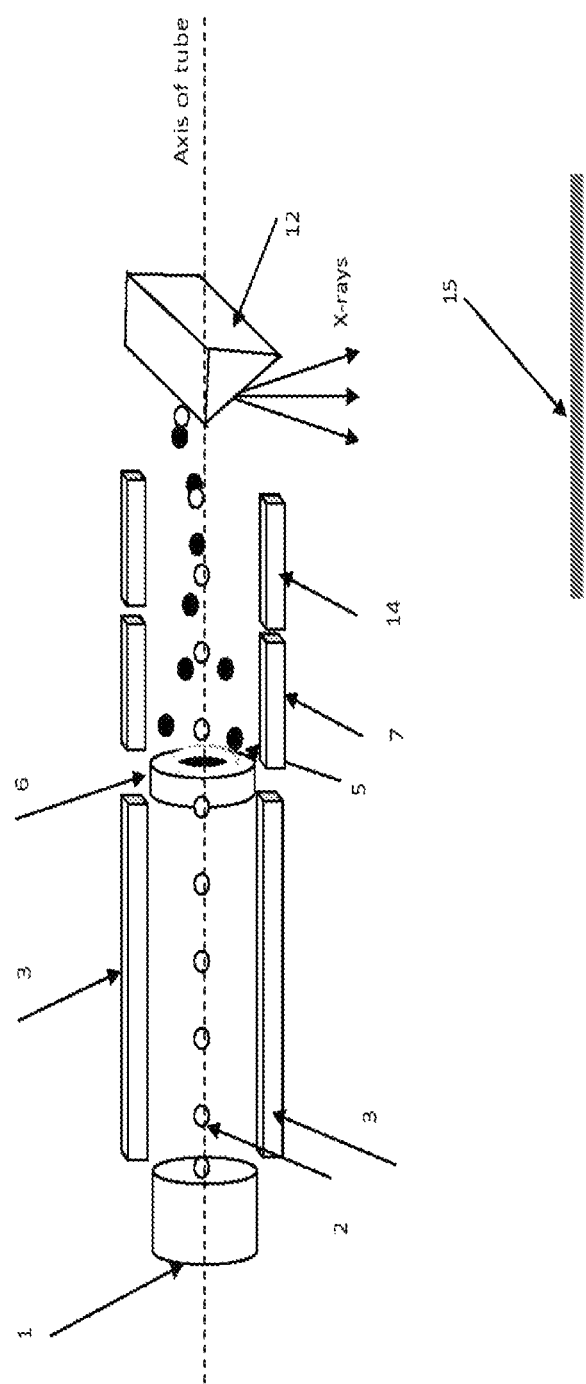
FIG. 10 shows the new source, with the scanning mechanism, and a detector 15. The detector can be an area detector, line scan detector, point detector or any suitable x-ray receptor.
Figure 11:
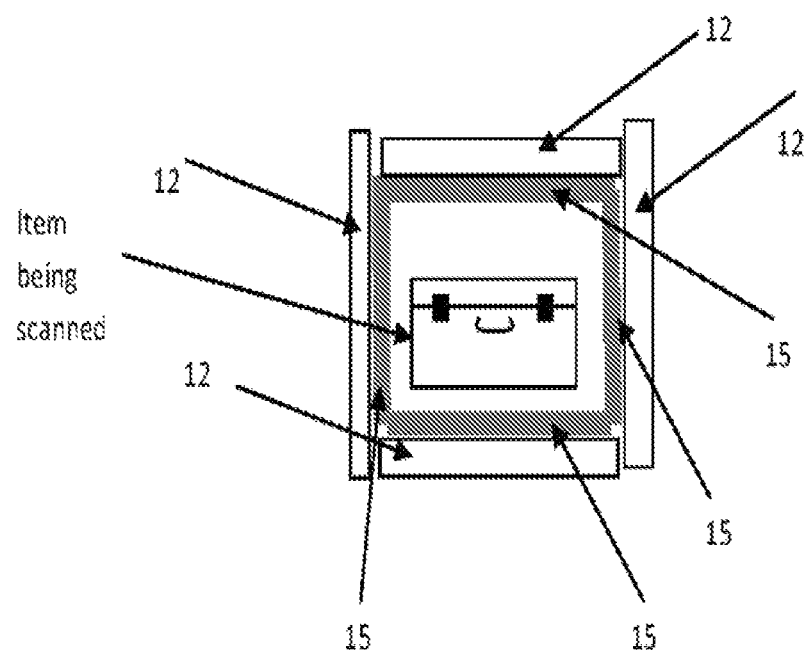
FIG. 11 shows the detector in FIG. 10, being used in a baggage and/or cargo scanning device that takes line scan, or tomographic images.
Figure 21:
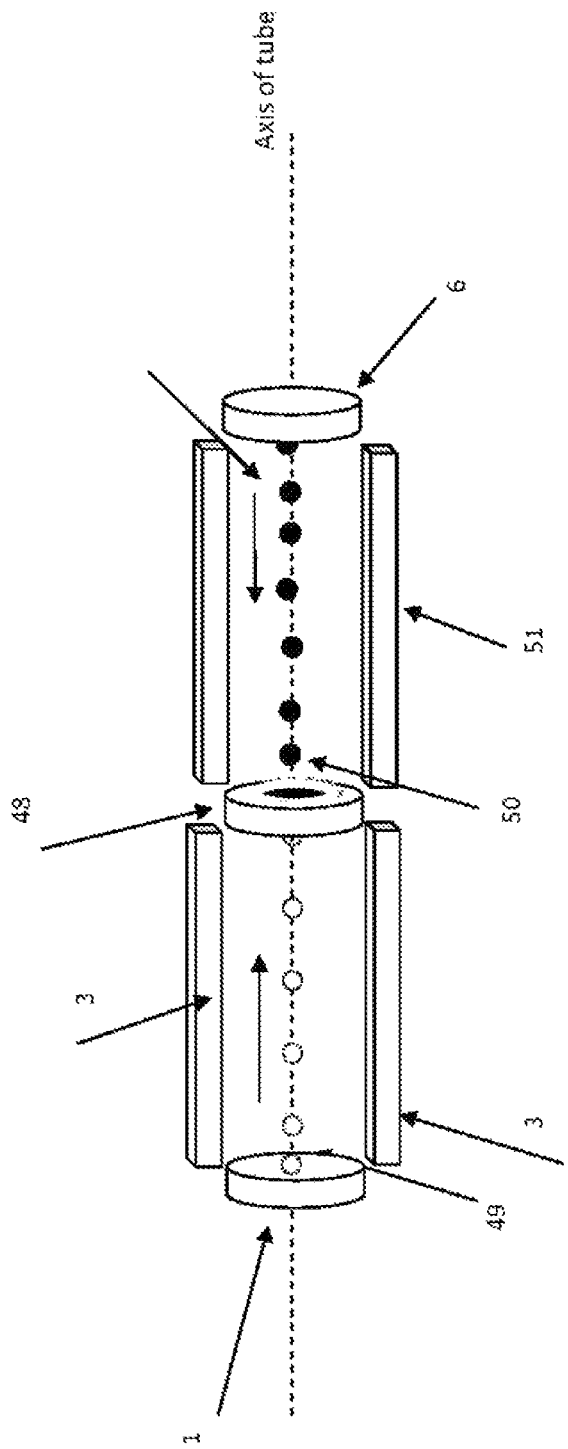
FIG. 21 shows a variation of the new source with the particles accelerating towards the center of the tube. One example could be for generating neutrons if deuterium or tritium, or other suitable particles are used. Each cathode can emit different materials, and/or can be made of different materials.
Figure 22:
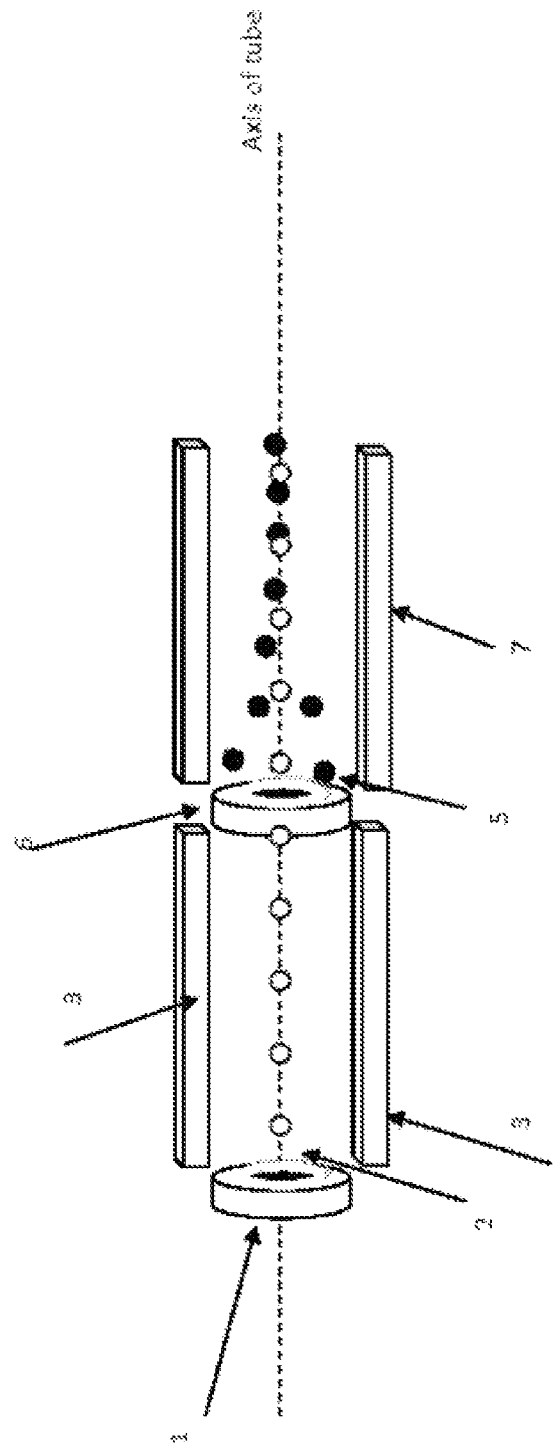
FIG. 22 shows a pictorial view of one embodiment, where the two energies to such things as betatrons, cyclotrons, and other devices that use injected electrons or particles are used. Multiple different energies and types of particles or electrons can be injected.

There are a number of variations of this source that can be developed. For example, more than two energy ranges can be output. Three, four, or more endpoint energy levels can be output by the system by using the approach shown in FIG. 4. The anode can be a rotating anode, a fixed anode, a transmission anode, or a reflecting anode. It is possible to combined several energies with several anode materials (or filters), as shown in FIGS. 7 and 8. Different materials, different combinations of materials, multiple material locations can be used on a rotating target as shown in FIG. 8. Different filtering material can be used on the back of the target, in both conventional targets and the rotating target. Multiple variations are possible to those skilled in the art. Scanning of the X-ray beam at different energies can be accomplished by methods that are well know and used in the industry, a variation of which is illustrated in FIG. 9 using deflection plates or coils 14. In FIG. 10, the scanning source is shown with a detector 15 that can be one or more line scan detectors, area detectors, energy discrimination detectors, point, phosphor, direct-detect, or some other X-ray detector. An example application of using the source in FIG. 10 is shown in FIG. 11, were the system is set up to screen cargo, baggage, or items of interest. In this case, a view down the baggage tunnel is shown, with scanning of baggage and cargo, as illustrated in FIG. 11. In this case, multiple dual energy sources are used to capture image data for a tomographic or laminographic reconstruction. The bag would move down the tunnel to capture the tomographic or transmission image data. FIG. 21 depicts alternate method of using an embodiment of the invention. In this case, the cathodes 1, 6 emit particles, and these particles collide in the middle at anode 48. In this case, the anode also has a hole such that the particles impact each other. Examples of this may be emitting deuterium in both cathodes, and the resulting collision would produce neutrons. Yet another variation is show in FIG. 22, where the anodes emit electrons or other particles. In this case, the embodiment is used as a multi-energy electron source. This may be used by such things as betatrons, cyclotrons, or a device that can use multiple energy particles or electrons, at high switching speeds or with the characteristics provided by this embodiment.

Figure 18:
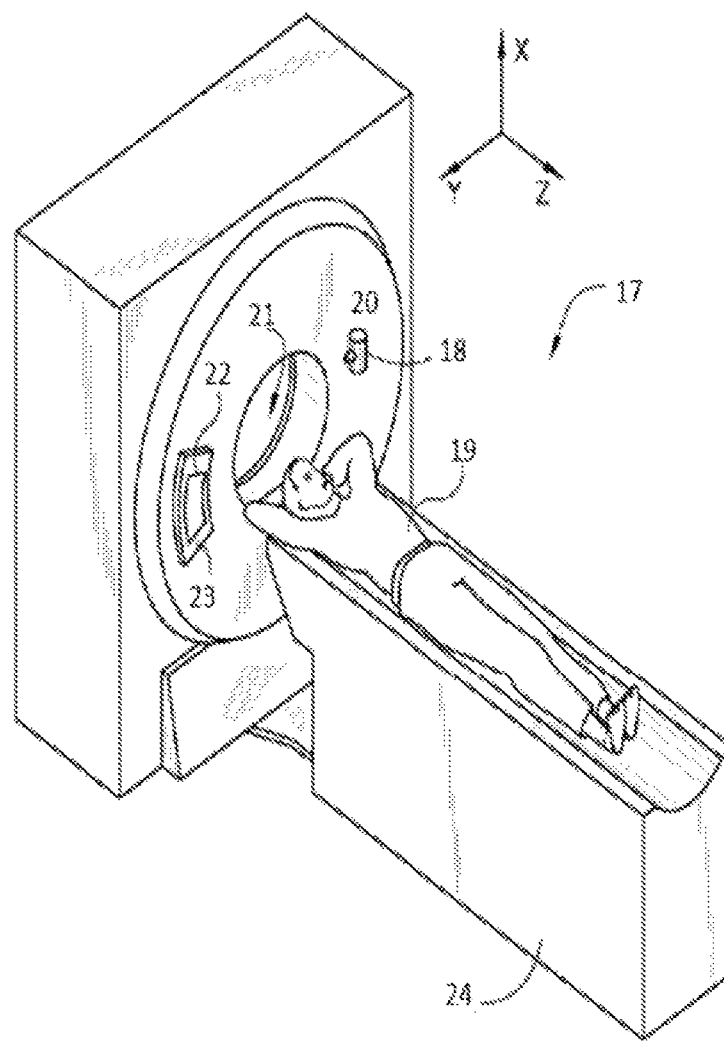
FIG. 18 shows a pictorial view of a CT imaging system.
Figure 19:
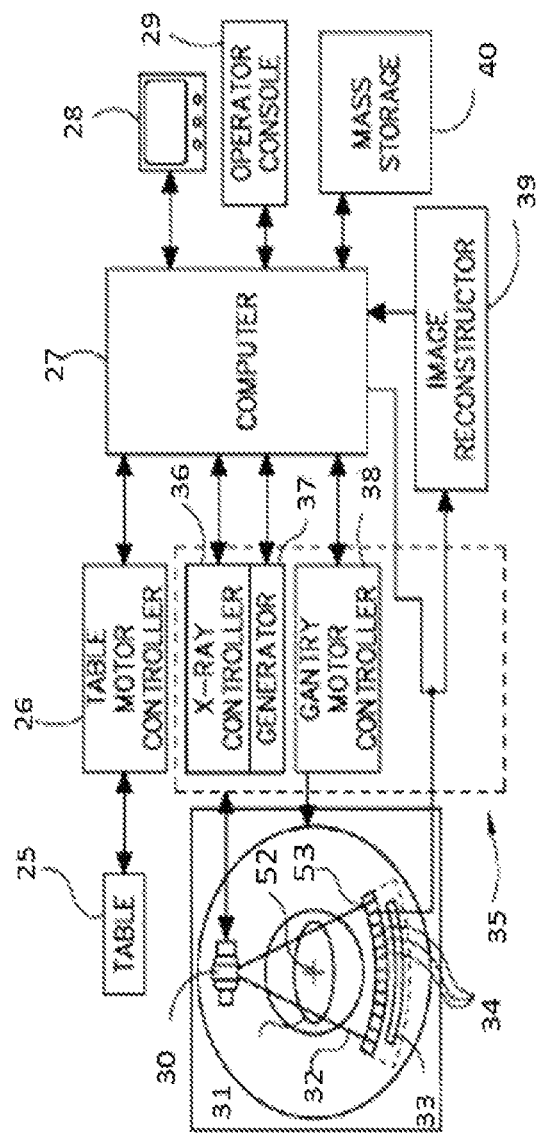
FIG. 19 shows a bock schematic diagram of the system illustrated in FIG. 18.

A more detailed description of how the system would work in a medical CT application is shown in FIGS. 18 and 19. Referring to FIG. 18, a computed tomography (CT) imaging system 17 is shown as including a gantry 20 representative of a "third generation" CT scanner. Gantry 20 has a dual energy x-ray source 18 that projects a beam of x-rays 32 toward a detector assembly or collimator 53 on the opposite side of the gantry 20. In some embodiments of the invention, x-ray source 18 includes either a stationary target or a rotating target. Referring now to FIG. 19, detector assembly 53 is formed by a plurality of detectors 34 and data acquisition systems (DAS) 33. The plurality of detectors 34 sense the projected x-rays that pass through a medical patient 19, and DAS 33 converts the data to digital signals for subsequent processing. Each detector 34 produces an analog electrical signal that represents the intensity of an impinging x-ray beam and hence the attenuated beam as it passes through the patient 19. During a scan to acquire x-ray projection data, gantry 20 and the components mounted thereon rotate about a center of rotation 52.

Rotation of gantry 20 and the operation of x-ray source 18 are governed by a control mechanism 35 of CT system 17. Control mechanism 35 includes an x-ray controller 36 and generator 37 that provides power and timing signals to an x-ray source 18 and a gantry motor controller 38 that controls the rotational speed and position of gantry 20. An image reconstructor 39 receives sampled and digitized x-ray data from DAS 33 and performs high speed reconstruction. The reconstructed image is applied as an input to a computer 27 which stores the image in a mass storage device 40.

Computer 27 also receives commands and scanning parameters from an operator via console 29 that has some form of operator interface, such as a keyboard, mouse, voice activated controller, or any other suitable input apparatus. An associated display 28 allows the operator to observe the reconstructed image and other data from computer 27. The operator supplied commands and parameters are used by computer 27 to provide control signals and information to DAS 33, x-ray controller 36 and gantry motor controller 38. In addition, computer 27 operates a table motor controller 26 which controls a motorized table 25 to position patient 19 and gantry 20. Particularly, table 25 moves patients 19 through a gantry opening 21 of FIG. 18 in whole or in part.

System 17 may be operated in one of the configurations detailed in this document. In operation, a potential is applied between the anode and cathodes, and electrons emitting from the cathodes are caused to accelerate, via the potential, toward the anode. For dual energy imaging, the grids are controlled such that one-energy is first output, this is turned off via the grid, and then, by varying the appropriate grid voltage, the next energy is output. The source is capable of very rapid switching speeds, and also it is possible to vary the flux from each energy. Thus the system rapidly switches energy and flux to captures dual energy X-ray image data. If desirable the system can be designed to vary the spot size. After or during the data capture, the image is filtered, reconstructed, and analyzed. Note that the detector does not have to capture the data in two energies, and can be used to capture the data in a single energy, or in two energies.

Figure 20:
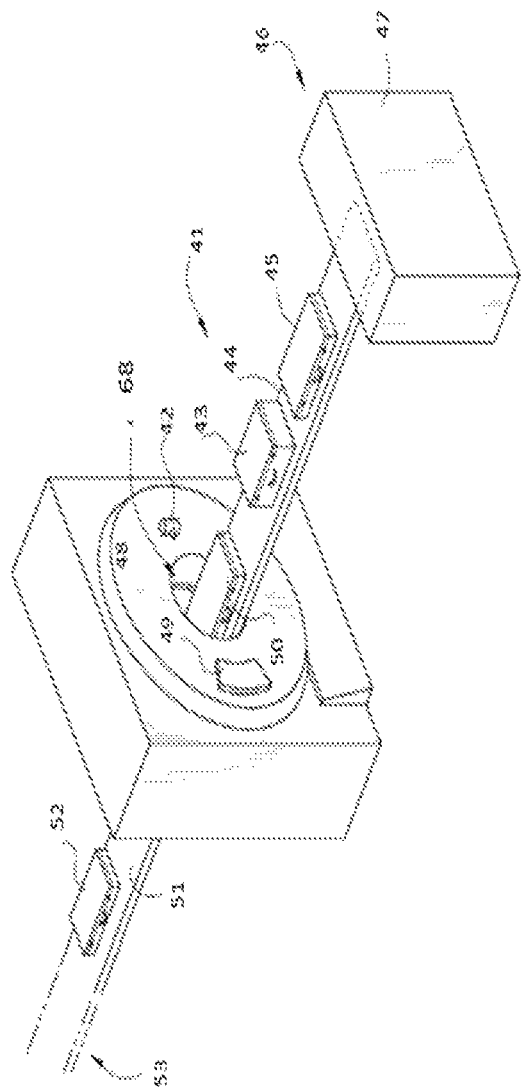
FIG. 20 shows a pictorial view of a CT system for use with a non-invasive package inspection system according to an embodiment of the invention.

FIG. 20 shows a package/baggage CT system that uses a rotating gantry instead of a stationary source as shown in FIGS. 10 and 11. Referring now to FIG. 20, package/baggage inspection system 41 includes a rotatable gantry 48 having an opening 68 therein through which packages or pieces of baggage may pass. The rotatable gantry 48 houses dual energy X-ray source 42 as well as a detector assembly 49. A conveyor system 53 also is provided and includes a conveyor belt 52 supported by structure 47 to automatically and continuously pass packages or baggage pieces 45 through opening 41 to be scanned. Objects 43 are fed through opening 68 by conveyor belt 51, imaging data is then acquired, and the conveyor belt 51 removes the packages 43 from opening 68 in a controlled and continuous manner. As a result, postal inspectors, baggage handlers, and other security personnel may non-invasively inspect the contents of packages 43 for explosives, knives, guns, contraband, etc.

An implementation of the system 17 and/or 41 in an example comprises a plurality of components such as one or more of electronic components, hardware components, and/or computer software components. A number of such components can be combined or divided in an implementation of the system 17 and/or 41. An exemplary component of an implementation of the system 17 and/or 41 employs and/or comprises a set and/or series of computer instructions written in or implemented with any of a number of programming languages, as will be appreciated by those skilled in the art. An implementation of the system 17 and/or 41 in an example comprises any (e.g., horizontal, oblique, or vertical) orientation, with the description and figures herein illustrating an exemplary orientation of an implementation of the system 17 and/or 41, for explanatory purposes.

An implementation of the system 17 and/or the system 41 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 17 and/or the system 41 comprises the recordable data storage medium of the image reconstructor 39, and/or the mass storage device 40 of the computer 27. A computer-readable signal-bearing medium for an implementation of the system 17 and/or the system 41 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 17 and/or the system 41, for instance, one or more of a telephone network, a local area network ("LAN"), a wide area network ("WAN"), the Internet, and/or a wireless network.

Figure 23:
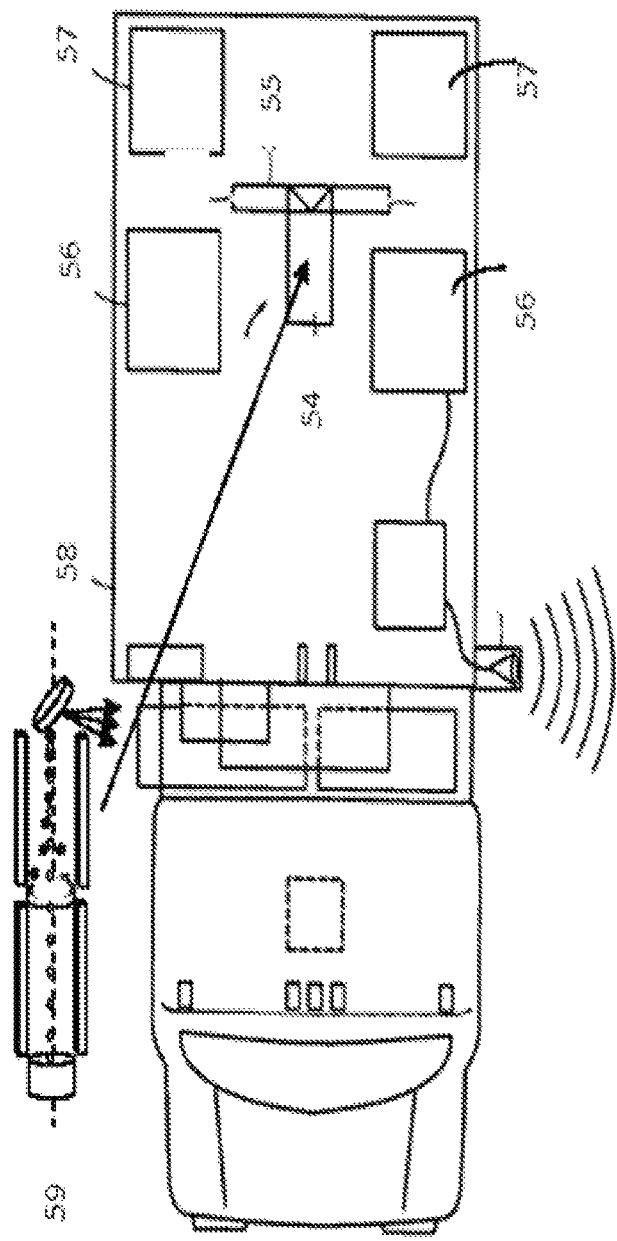
FIG. 23 shows a pictorial view of a backscatter van, using multiple energies according to an embodiment of the invention.
Figure 24:
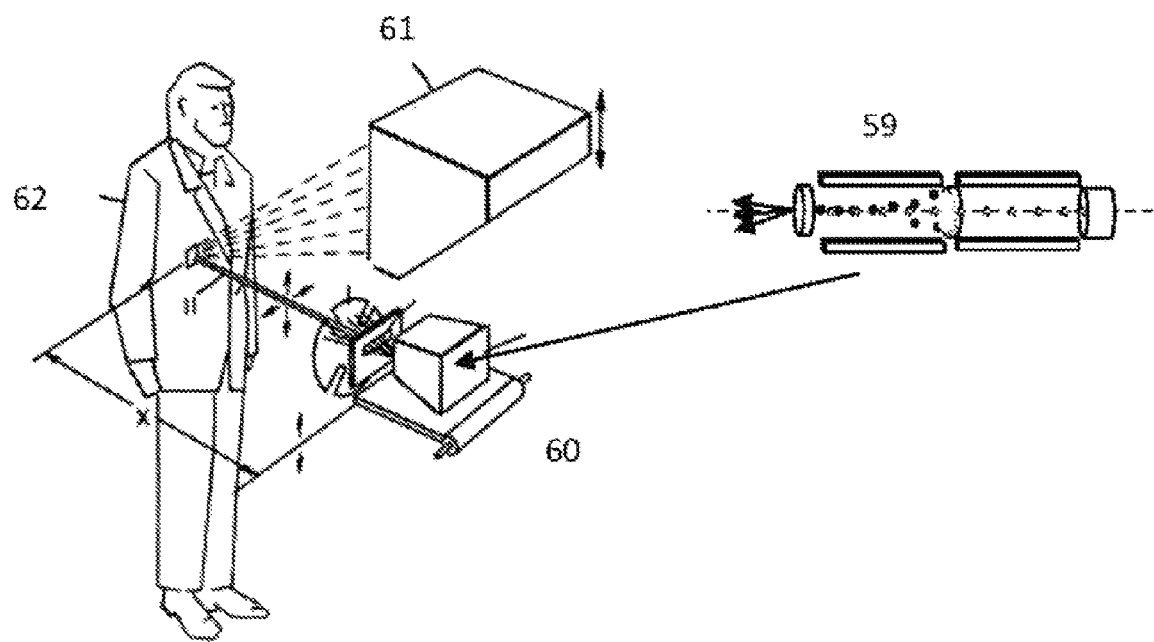
FIG. 24 shows a pictorial view of a backscatter body imaging system that can use two or more energies, according to an embodiment of the invention.

FIG. 23 depicts the X-ray source being used in a backscatter van. Here the dual or multi energy source 59 can be used to provide additional backscatter energies from the scanning. The van 58 has multiple detectors 56, 57. The flying spot mechanism 54 includes the source 59 and the chopper wheel 55. The Van 58 can be configured to emit X-rays from either side of the van. Typical operation would be to scan one pixel and one energy, and then to scan the next location using the next energy. This results two images with different energies. As the new source 59 can rapidly switch energies and flux, the capture rate of the detector 56, 57 can potentially be increased to get the desired resolution. In addition, the flux from the different energies can be dynamically adjusted to improve the resulting image signal to noise. FIG. 24 shows a backscatter X-ray body imaging device. The use of this new source 59 provides the ability to replace the current source, thus providing the ability to capture multiple-energy x-ray images. The associated detector 61 and person being scanned 62 are shown. Multiple different variations for backscatter imaging is possible, in addition to the one shown in FIG. 24. In addition to providing dual or multiple energies, it is possible by adjusting the spot locations, for example from side to side, to increase the information from the system.

Figure 25:
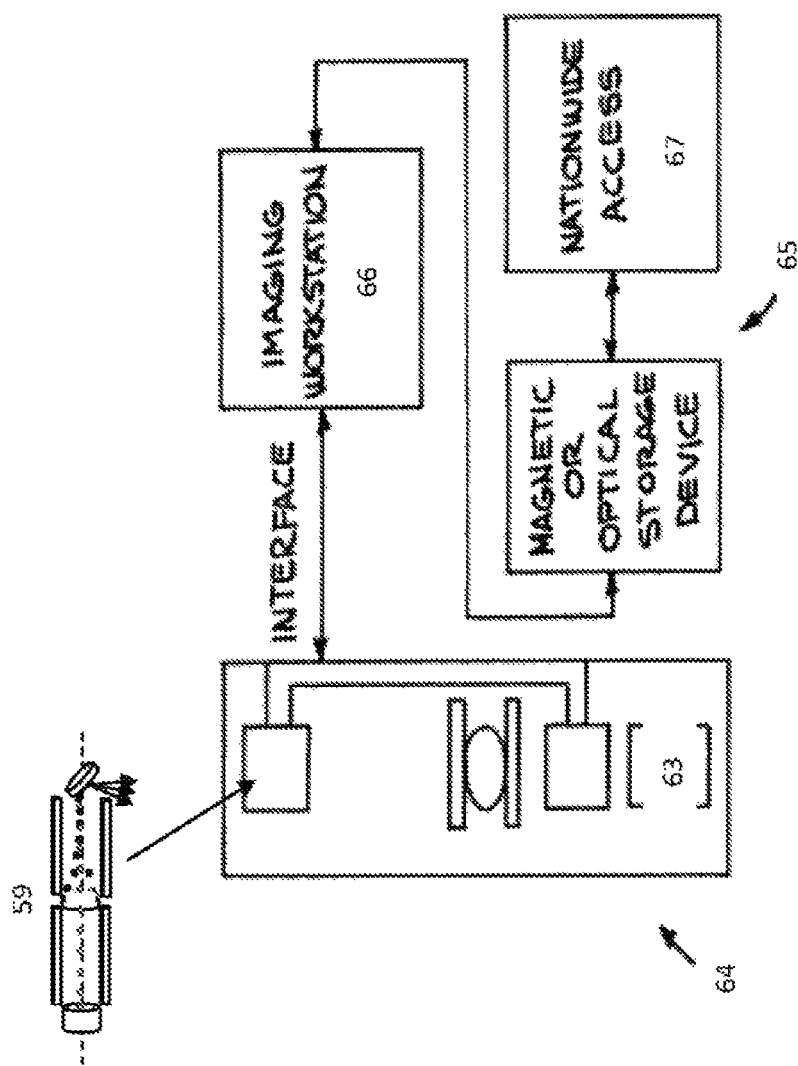
FIG. 25 shows a pictorial view and block diagram of an embodiment being used for mammography.

FIG. 25 shows a pictorial representation of a mammography system. The system basically comprises an X-ray mammography unit 64, detector(s) 63 and imaging work station 66 and an image library 65. The X-ray mammography unit 64 includes the x-ray generator and source 59, which can have multiple configurations as detailed in this document. With this embodiment, the X-ray tube output energies, flux, anode materials, multiple anode materials, spot size and filters for the X-rays can be varied, to get the desired characteristics out of the resulting images. By adjusting the spot location, or by having two or more spot locations, it is possible to use this source to provide limited angle tomography/laminography. There are various different ways to do this, for example with electron optics, the focus, deflection plates or coils 14, or by physically moving the source.

Figure 26:
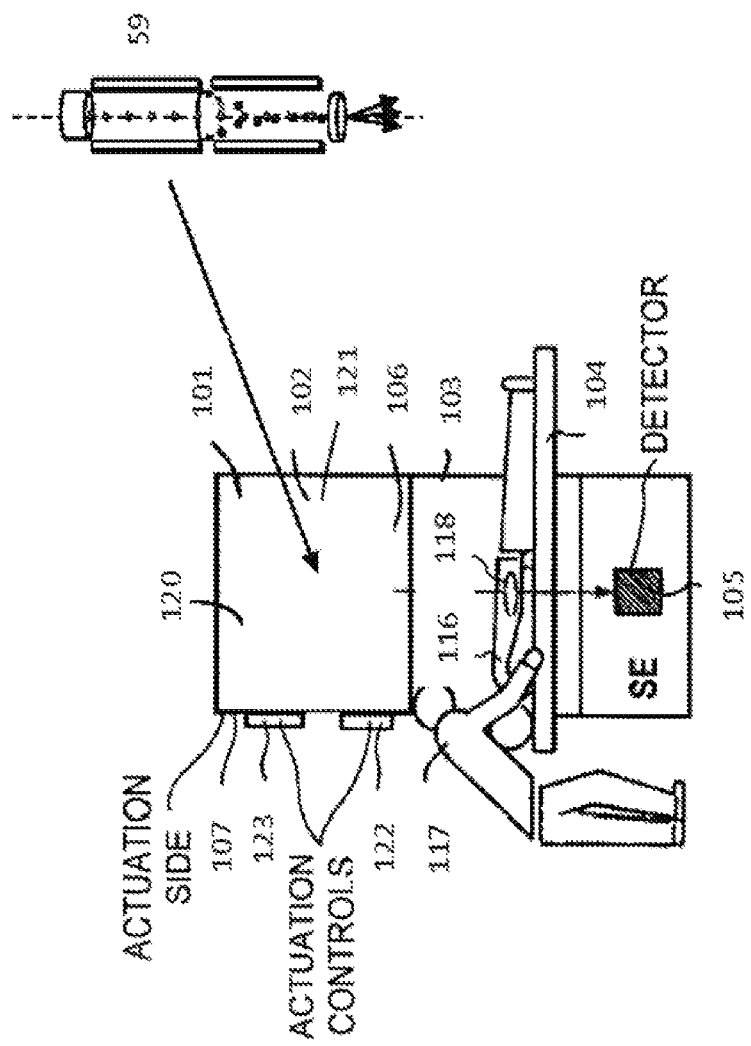
FIGS. 26 and 27 shows a pictorial view of an embodiment being used for radiography.

FIG. 26 show a conventional radiography imaging system. In this system, the patient 116 can be moved forward or back, and the source 59 and detectors 105 may be adjustable. One or more detectors 105 is used to capture the image. The dual energy x-ray source 59 can be used in these cases to provide very stable output energy in one, two, or multiple energies. As with all other configurations, the tube energy, anode material (s), flux, spot size, and filters can be adjusted to get the desired characteristics out of the system. By varying the spot size, the system resolution can be varied. In addition, by moving the electron spot location, it is possible to produce limited angle tomography/laminography. Example methods to produce 3D information would be to capture the image using different spot locations, for example with electron optics, the focus, deflection plates or coils 14, or by physically moving the source.

Figure 27:
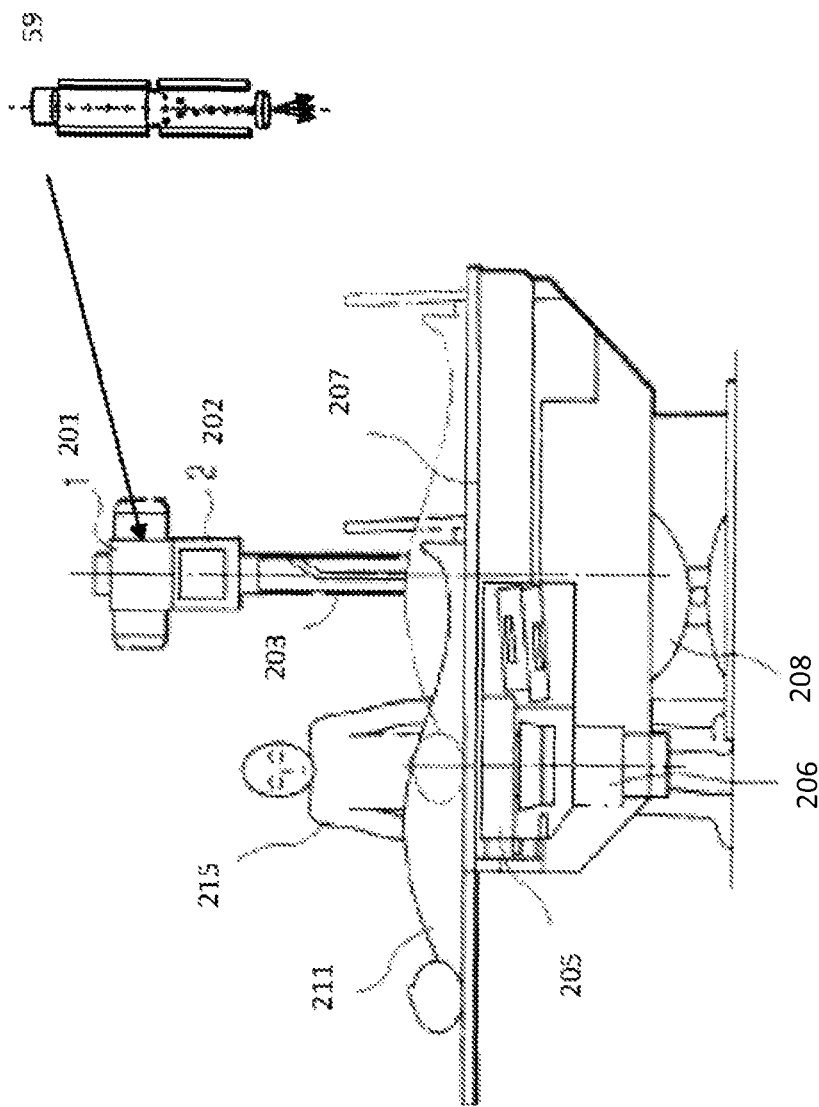

Another example shown in FIG. 27 shows the operation of the X-ray fluoroscopic and radiographic apparatus in which the operator 215 approaches the table top board 207 from the back side of the X-ray fluoroscopic and radiographic apparatus.

First, the X-ray fluoroscopic and radiographic apparatus is set at a horizontal posture. Since the mechanism is composed in such a manner that the X-ray tube 59 and the image receiving system 205 are moved independently from each other, a focal position of the X-ray tube 59 and a tube axis of the image intensifier 206 of the image receiving systems are made to coincide with each other by a controller. Then, X-rays are irradiated from the X-ray tube 59, and an X-ray image formed on a monitor is adjusted in a necessary field of view by the collimator 202. Next, the subject person 211 is put on the table top board 207. Then, X-rays are irradiated again. While observing an X-ray fluoroscopic image formed on the monitor, the operator 215 operates a handle on a control panel of the controller and moves the table top board 207 in the direction of X-Y so that a target portion of the subject person 211 can be positioned at the center on the monitor. At this time, X-ray spot radiography is conducted if necessary.

X-rays are turned off. Depending upon a portion to be diagnosed, marking is made by an illuminating lamp in the target portion on a body surface of the subject person 211. Then, the table top board 207 is moved to a position close to the support column 203 above the main frame 204, and the support column 203 supporting the X-ray tube 59 is moved to a lower side in a longitudinal direction of the table top board 207. At this moment, a space occupied by the support column 203 becomes open. Therefore, it is possible for the operator 215 to approach a position very close to the table top board 207 from the back side of the apparatus. Therefore, in addition to the X-ray fluoroscopic diagnosis, it is possible to conduct other diagnoses such as an endoscope diagnosis and ultrasonic wave diagnosis at the same time.

In the X-ray fluoroscopic and radiographic apparatus, the image receiving system 205 can approach a position distant from an end of the upper side (head portion of the subject person) of the table top board 207, for example, by 38 cm. The operator 215 approaches a front side or the back side of the table top board 207 and conducts an endoscope inspection while monitoring a fluoroscopic image of the head portion of the subject person with the help of an assistant or nurse. Alternatively, the urinary organ inspection (radiography of the kidney and urethra system with a contrast medium) is conducted as follows. While legs of the subject person are arranged on the upper side of the table top board 211, a nurse approaching the table top board 207 injects a contrast medium into the vein of the subject person, and an X-ray inspection engineer conducts a spot-radiography at regular intervals. In order to conducts those inspections, it is necessary for the operator 215, assistant, nurse and X-ray inspection engineer to prepare for the inspection of the subject person 211 around him. Therefore, on this X-ray fluoroscopic and radiographic apparatus, it is possible to make a space when the support column 203 is moved in the longitudinal direction of the table top board 207. Further, it is possible to move the back side portion of the table top board 207 to a position close to the support column above the main frame 204. Therefore, the operator 215 can come to an end of the table top board 207 to conduct the inspection work.

An embodiment of an X-ray fluoroscopic and radiographic apparatus is composed as described above. When an image is captured, one two energy images can be captured. Similarly, K-edge imaging can be done by suitably selecting the energies and/or filters, anode material and other tube configurations. Alternately different spot sizes can be used. The support column for holding the X-ray tube is held on a side of the main frame, and the support column and the image receiving system are mechanically connected with each other and moved in the longitudinal direction of the table top board, or alternatively the support column and the image receiving system are independently moved in the longitudinal direction of the table top board. When the support column is moved, a space occupied by the support column becomes open, and further the table top board can be moved to a position close to the support column above the main frame. Therefore, it is possible for the operator to approach an end of the table top board and easily make a diagnosis for the subject person while the operator is being kept in an easy body orientation.

Figure 30:
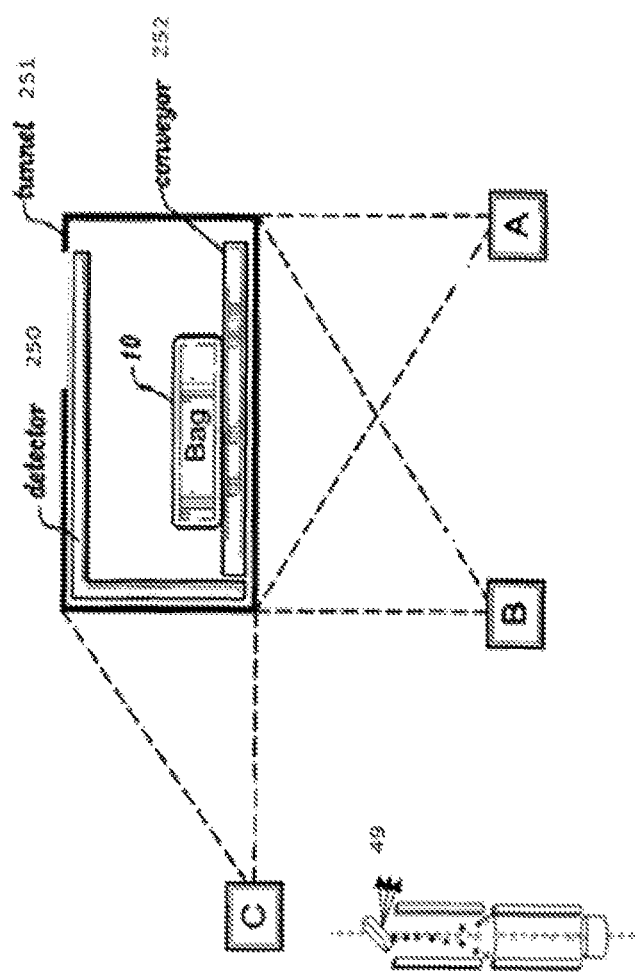
FIG. 30 shows a multi-view x-ray system used to screen baggage. A,B,C are the respective X-ray sources.

FIG. 30 shows another example of the X-ray source, but in a multi view X-ray system, that is used at security checkpoints. One or more X-ray sources 59 can be used. Locations A, B, C are potential locations for the source, if the system uses three images. Typically each x-ray generator 59 would have an associated detector 250. In this case the baggage would travel down the tunnel 251, being carried by the conveyor 252.

These previous examples provide are a few examples of how the different sources can be used, and those skilled in the art will recognize that there are many different variations, including conventional single view X-ray used at security checkpoints, dual energy car scanning devices, k-edge imaging, laminography, tomography, microfocus imaging, multiple spot-size imaging, or tomosynthesis using a scanning electron beam, XRF applications, XRD applications, XRF or XRD imaging, and any application that uses dual or multiple energy or energy range X-rays.

Associated with embodiments in this document, but known to those skilled in the art is the associated detectors, computer, and the hardware and software to do the capture, filter, reconstruction, analysis and display of the resulting images, measurements or output from the device for using the dual energy X-ray source. This has been mentioned in several cases, but is well known to those skilled in the art.

With regards to the power supply, the power supply for the source can be constructed in many different ways by those skilled in the art.

Figure 12:
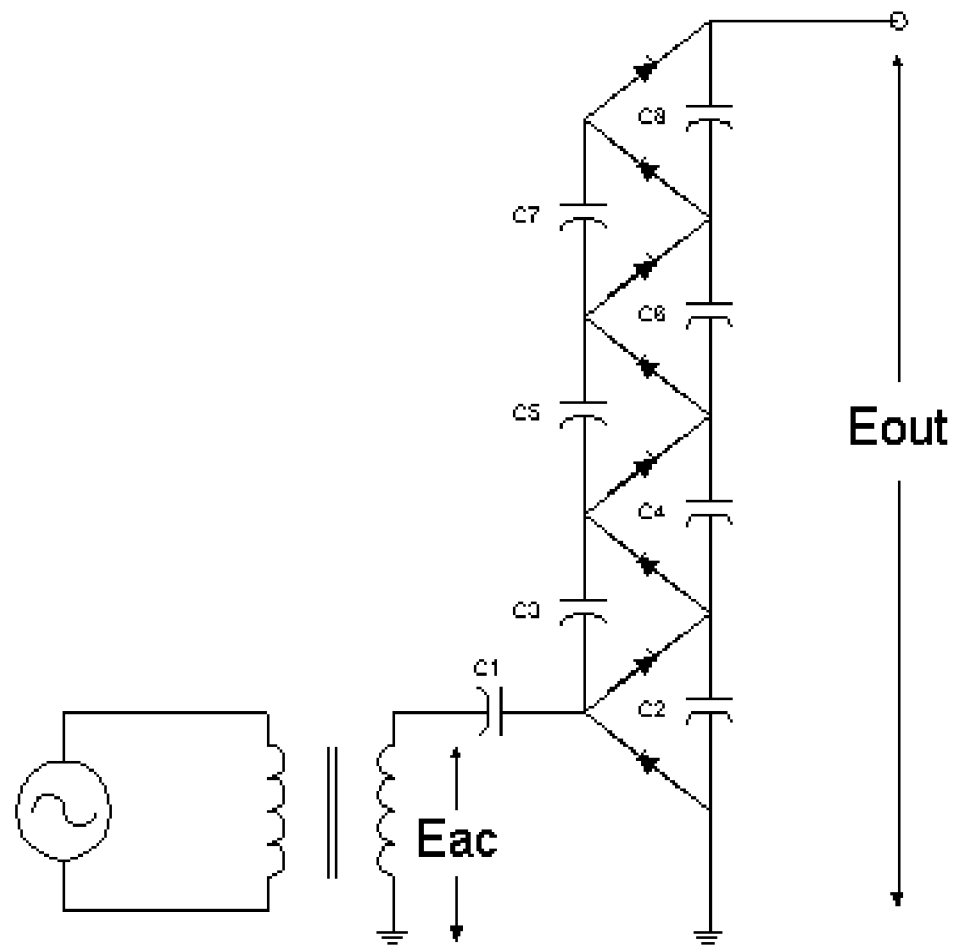
FIG. 12 shows a half wave Cockcroft Walton multiplier.
Figure 13:
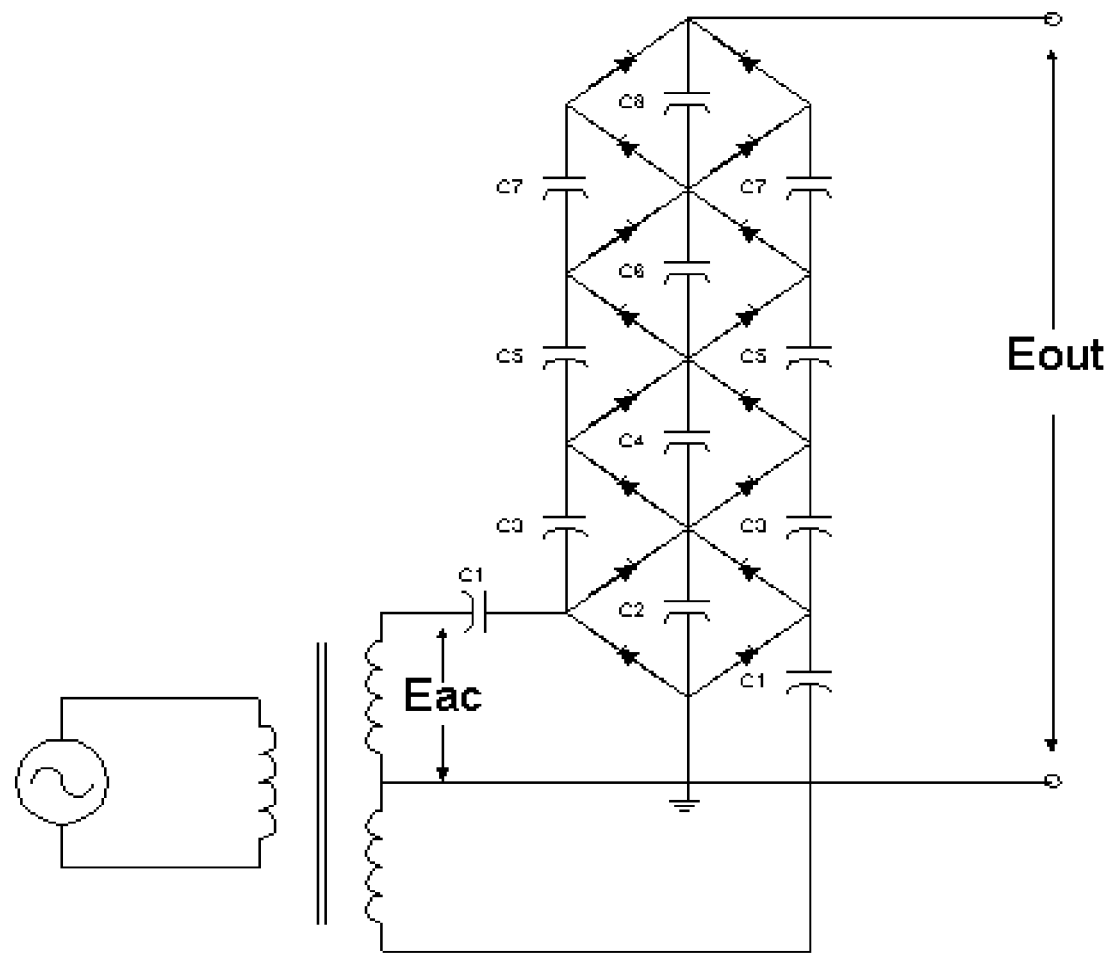
FIG. 13 shows a full wave Cockcroft Walton multiplier.
Figure 14:
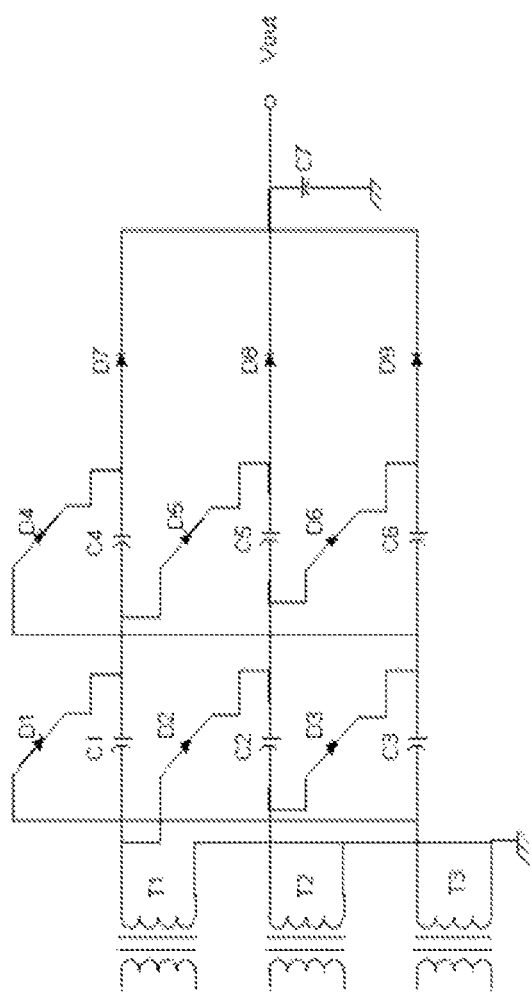
FIG. 14 shows a three phase multiplier circuit.
Figure 15:
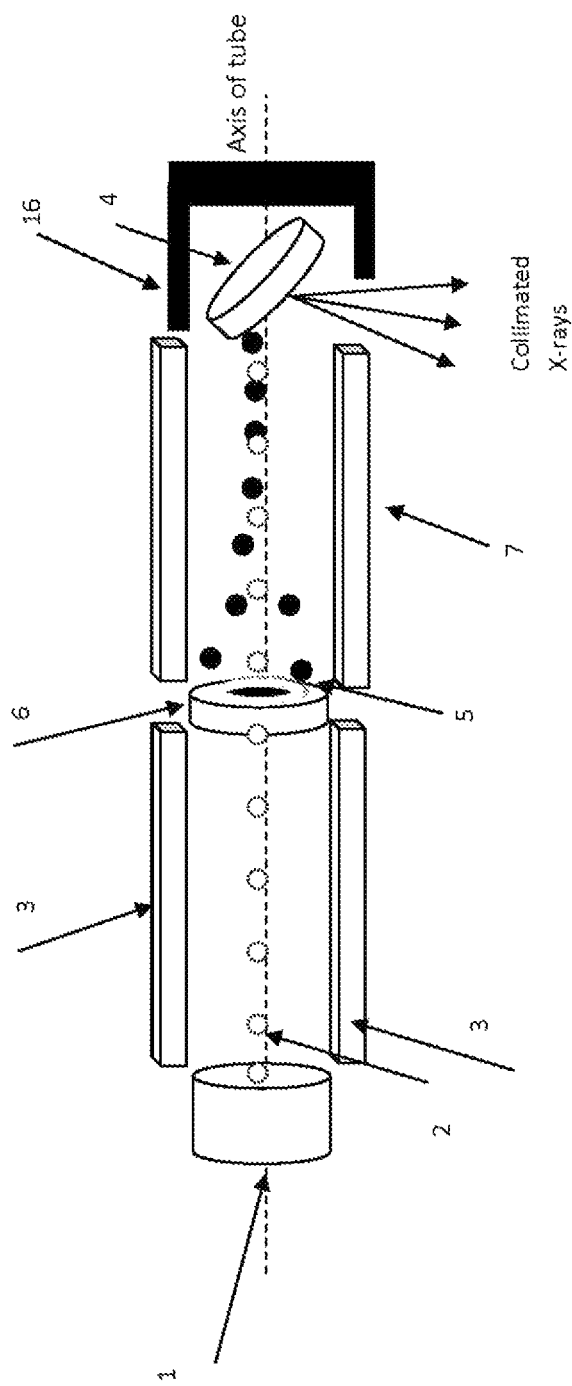
FIG. 15 shows an embodiment with shielding/collimation 16 around the anode.
Figure 16:
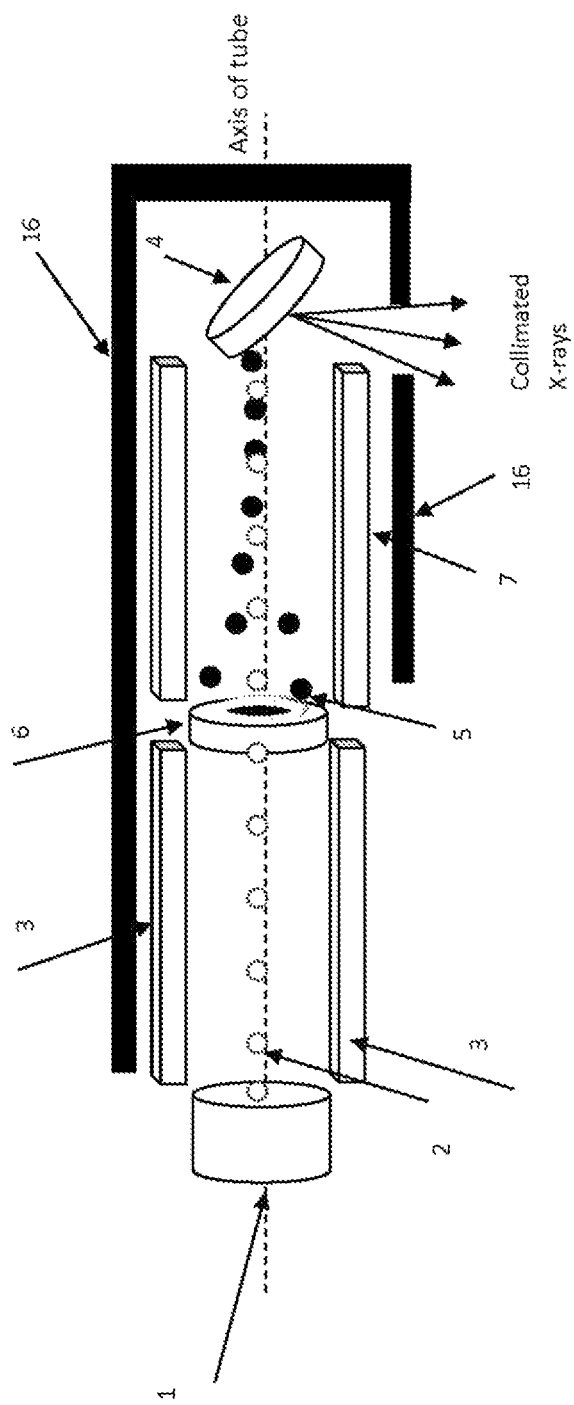
FIG. 16 shows an embodiment with shielding/collimation 16 around the anode and grid, but inside the tube. Alternately this shielding can be outside the tube.
Figure 17:
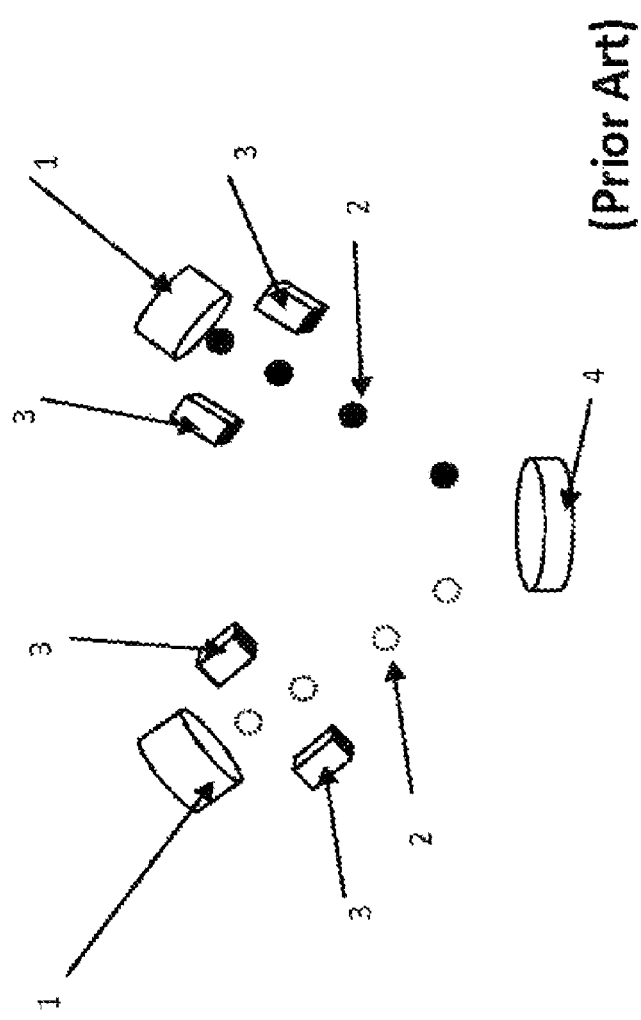
FIG. 17 shows prior art of dual energy X-ray source with two cathodes and one anode.

One way of getting the desired voltages is by tapping off the appropriate multiplier level of a voltage multiplier. A half-wave Cockcroft Walton (CW) multiplier is shown in FIG. 12, a Full Wave multiplier for higher current is shown in FIG. 13, and a three phase multiplier is shown in FIG. 14. Still another example for a dual energy X-ray tube, the power supply may be a Peschel design with multiple transformers stacked on the top of each other.

Ideally, for very stable Source output, there will be a closed loop feedback mechanism for each stage. Thus the output stages are tapped off the appropriate multiplier level, and the resulting voltage on the accelerating stage and/or cathode are measured, and closed loop feedback is used to control each stage. Additional acceleration stages can also be added to ensure smooth acceleration of the electrons.

While the invention has been described in detail in connection with only a limited number of embodiments, it should be readily understood that the invention is not limited to such disclosed embodiments. Rather, the invention can be modified to incorporate any number of variations, alternations, substitutions, or equivalent arrangements not hereto for described, but which are commensurate with the spirit and scope of the invention. Furthermore, the invention is applicable to any device that accelerates positively or negatively charged particles, sub atomic particles, or ions. Accordingly, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A source device comprising:
   a chamber;
   a first cathode positioned within the chamber;
   a second cathode positioned within the chamber; and
   an anode positioned within the chamber;
   wherein the first cathode is separated from the anode in a direction at least partially along an axis of the chamber by a first distance, the second cathode is separated from the anode in the direction at least partially along the axis of the chamber by a second distance, and wherein the first distance is smaller than the second distance; and
   wherein the first cathode comprises an opening through which charged particles emitted by the second cathode can pass.

2. The source of claim 1, wherein the opening is oriented about the axis of the chamber.

3. The source of claim 1, wherein the first cathode is positioned at least partially off of the axis of the chamber.

4. The source of claim 3, wherein the second cathode is positioned at least partially on the axis of the chamber.

5. The source of claim 1, further comprising a grid configured to control movement of charged particles in the chamber.

6. The source of claim 1, further comprising:
   a first grid configured to control movement of charged particles between the first cathode and the anode; and
   a second grid configured to control movement of charged particles between the second cathode and the first cathode.

7. The source of claim 6, wherein the first and second grids are configured to direct charged particles from the first and second cathodes towards a single spot location on the anode.

8. The source of claim 6, wherein the first grid is configured to direct charged particles from the first cathode towards a first spot location on the anode and to direct charged particles from the second cathode towards a second spot location on the anode.

9. The source of claim 1, further comprising a power supply configured to supply a first potential difference between the first cathode and the anode and to supply a second potential difference between the second cathode and the anode.

10. The source of claim 9, wherein the first and second potential differences are different in magnitude or polarity.

11. The source of claim 1, wherein the first and second cathodes are configured to emit charged particles in a direction along an axis of the chamber.

12. The source of claim 1, wherein the chamber is a tube.

13. The source of claim 1, further comprising a focus configured to control the flow of charged particles in the chamber.

14. The source of claim 1, further comprising a deflection plate configured to control the flow of charged particles in the chamber.

15. The source of claim 1, further comprising a coil configured to control the flow of charged particles in the chamber.

16. The source of claim 1, wherein the first and second cathodes are configured to emit electrons.

17. An X-ray source comprising:
   a chamber having an axis;
   a first cathode positioned within the chamber and configured to emit charged particles;
   a second cathode positioned within the chamber and configured to emit charged particles;
   an anode positioned within the chamber;
   a first grid configured to cause charged particles from the first cathode to move at least partially along the axis of the chamber; and
   a second grid configured to cause charged particles from the second cathode to move at least partially along the axis of the chamber;
   wherein the first cathode is separated from the anode in a direction at least partially along an axis of the chamber by a first distance, the second cathode is separated from the anode in the direction at least partially along the axis of the chamber by a second distance, and wherein the first distance is smaller than the second distance; and
   wherein the first cathode comprises an opening through which charged particles emitted by the second cathode can pass.

18. An X-ray machine comprising:
   an X-ray source comprising
      a tube,
      a first cathode positioned within the tube and configured to emit electrons, the first cathode comprising an opening,
      a second cathode positioned within the tube and configured to emit electrons,
      an anode positioned within the tube,
      a grid configured to direct charged particles from the second cathode through the opening in the first cathode; and
   an X-ray detector.

19. An X-ray source, the source comprising,
   a chamber;
   a first cathode positioned within the chamber and configured to emit electrons, the first cathode comprising an opening;
   a second cathode positioned within the chamber and configured to emit electrons,
   an anode positioned within the chamber; and
   a grid configured to direct the electrons from the second cathode through the opening in the first cathode.

20. The X-ray source of claim 19, wherein the chamber is a tube.

* * * * *